(12) United States Patent
Schraut et al.

(10) Patent No.: US 10,239,818 B2
(45) Date of Patent: *Mar. 26, 2019

(54) METHOD FOR PRODUCING DIESTERS OF TEREPHTHALIC ACID WITH CIRCULATION OF THE REACTION MIXTURE

(71) Applicant: BASF SE, Ludwigshafen (DE)

(72) Inventors: Armin Schraut, Bensheim (DE); Martin Kaller, Mannheim (DE); Rob Bronneberg, Wattenheim (DE); Jasmin Stammer, Freinsheim (DE); Martin Das, Mannheim (DE); Gerrit Harnischmacher, Mannheim (DE)

(73) Assignee: BASF SE, Ludwigshafen Am Rhein (DE)

(*) Notice: Subject to any disclaimer, the term of this patent is extended or adjusted under 35 U.S.C. 154(b) by 0 days.

This patent is subject to a terminal disclaimer.

(21) Appl. No.: 15/513,716

(22) PCT Filed: Sep. 21, 2015

(86) PCT No.: PCT/EP2015/071574
§ 371 (c)(1),
(2) Date: Mar. 23, 2017

(87) PCT Pub. No.: WO2016/046117
PCT Pub. Date: Mar. 31, 2016

(65) Prior Publication Data
US 2017/0297996 A1 Oct. 19, 2017

(30) Foreign Application Priority Data
Sep. 24, 2014 (EP) .................................... 14186141

(51) Int. Cl.
*C07C 67/08* (2006.01)
*C07C 67/54* (2006.01)

(52) U.S. Cl.
CPC .............. *C07C 67/08* (2013.01); *C07C 67/54* (2013.01)

(58) Field of Classification Search
None
See application file for complete search history.

(56) References Cited

U.S. PATENT DOCUMENTS

| | | | |
|---|---|---|---|
| 2,825,738 A | 3/1958 | Ellendt et al. | |
| 4,372,857 A | 2/1983 | Matthews et al. | |
| 4,407,662 A | 10/1983 | Ginder | |
| 5,792,651 A | 8/1998 | Colpan et al. | |
| 6,699,386 B2 | 3/2004 | Todokoro et al. | |
| 6,916,950 B2 | 7/2005 | Gubisch et al. | |
| 7,276,621 B2 | 10/2007 | Cook et al. | |
| 7,385,075 B2 | 6/2008 | Disteldorf et al. | |
| 7,714,111 B2 | 5/2010 | Sun et al. | |
| 7,799,942 B2 | 9/2010 | Osborne et al. | |
| 8,034,970 B2* | 10/2011 | Hassan | B01F 7/00766 560/76 |
| 8,729,292 B2 | 5/2014 | Friese et al. | |
| 9,260,373 B2 | 2/2016 | Disteldorf et al. | |
| 2007/0161815 A1 | 7/2007 | Osborne et al. | |
| 2008/0139760 A1* | 6/2008 | DeBruin | B01D 3/14 526/67 |
| 2011/0251420 A1 | 10/2011 | Disteldorf et al. | |
| 2014/0148612 A1 | 5/2014 | De Munck et al. | |
| 2016/0264509 A1 | 9/2016 | Kaller et al. | |
| 2017/0044085 A1 | 2/2017 | Kaller et al. | |

FOREIGN PATENT DOCUMENTS

| | | |
|---|---|---|
| EP | 142157 A2 | 5/1985 |
| EP | 158754 A1 | 10/1985 |
| EP | 205582 A1 | 12/1986 |
| EP | 233692 A1 | 8/1987 |
| EP | 0407037 B1 | 1/1991 |

(Continued)

OTHER PUBLICATIONS

International Preliminary Examination Report with Applicant's Response (in German) for PCT/EP2015/071576 dated Dec. 7, 2016.
International Search Report for PCT/EP2015/071574 dated Dec. 17, 2015.
International Search Report for PCT/EP2015/071576 dated Dec. 17, 2015.
International Search Report for PCT/EP2015/071578 dated Dec. 21, 2015.
International Search Report for PCT/EP2015/071579 dated Jan. 8, 2016.

(Continued)

*Primary Examiner* — Ana Z Muresan
(74) *Attorney, Agent, or Firm* — Drinker Biddle & Reath LLP

(57) ABSTRACT

The present invention relates to a process for preparing a terephthalic diester by reacting terephthalic acid with at least one alcohol, wherein terephthalic acid is suspended in the alcohol in a dispersing tank, the preliminary suspension is passed from the dispersing tank into a reactor and converted in the presence of an esterification catalyst, a reaction suspension is drawn off from a region between the upper region and the lower region of the reactor, a first stream of the reaction suspension is recycled into the upper region of the reactor and a second stream of the reaction suspension is introduced into the lower region of the reactor, and the reaction suspension is thus mixed, wherein the stream drawn off and/or the first stream is passed through a heat exchanger outside the reactor and heated; and water of reaction is distilled off together with the vapor as alcohol-water azeotrope, the vapor is at least partly condensed, the condensate is separated into an aqueous phase and an organic phase and the organic phase is at least partly recycled into the reaction system.

14 Claims, 2 Drawing Sheets

(56) References Cited

FOREIGN PATENT DOCUMENTS

| | | |
|---|---|---|
| EP | 1186593 A2 | 3/2002 |
| FR | 2719039 A1 | 10/1995 |
| GB | 2088739 A | 6/1982 |
| GB | 2151501 A | 7/1985 |
| JP | H04308543 A | 10/1992 |
| JP | 2007077041 A | 3/2007 |
| JP | 49564945 | 6/2012 |
| WO | WO-8603686 A1 | 7/1986 |
| WO | WO-9521178 A1 | 8/1995 |
| WO | WO-99063076 A1 | 12/1999 |
| WO | WO-2005003152 A1 | 1/2005 |
| WO | WO-2005111059 A2 | 11/2005 |
| WO | WO-2007115046 A1 | 10/2007 |
| WO | WO-2010076192 A1 | 7/2010 |
| WO | WO-2010076193 A1 | 7/2010 |
| WO | WO-2012025308 A1 | 3/2012 |

OTHER PUBLICATIONS

Written Opinion of the International Searching Authority for PCT/EP2015/071574 dated Dec. 17, 2015.
Written Opinion of the International Searching Authority for PCT/EP2015/071578 dated Dec. 21, 2015.
Written Opinion of the International Searching Authority for PCT/EP2015/071579 dated Jan. 8, 2016.
English Translation of International Preliminary Report on Patentability for International Application No. PCT/EP2015/071574, dated Dec. 7, 2016.
U.S. Appl. No. 15/513,757, filed Mar. 23, 2017.
U.S. Appl. No. 15/513,730, filed Mar. 23, 2017.
U.S. Appl. No. 15/513,775, filed Mar. 23, 2017.

* cited by examiner

METHOD FOR PRODUCING DIESTERS OF TEREPHTHALIC ACID WITH CIRCULATION OF THE REACTION MIXTURE

CROSS-REFERENCE TO RELATED APPLICATIONS

This application is a national stage application (under 35 U.S.C. § 371) of PCT/EP2015/071574, filed Sep. 21, 2015, which claims benefit of European Application No. 14186141.9, filed Sep. 24, 2014, both of which are incorporated herein by reference in their entirety.

The invention relates to a process for preparing terephthalic diesters by reacting terephthalic acid with at least one alcohol.

Esters of terephthalic acid find use as plasticizers and are notable for favorable toxicological properties.

It is known that carboxylic acids can be prepared by reacting carboxylic acids with alcohols. This reaction can be conducted autocatalytically or catalytically, for example by means of Brønsted or Lewis acids. Irrespective of the manner of catalysis, the result is always a temperature-dependent equilibrium between the feedstocks (carboxylic acid and alcohol) and the products (ester and water).

In order to shift the equilibrium in favor of the ester (or of the full ester in the case of polybasic acids), an azeotroping agent is generally used, which helps to remove the water of reaction from the mixture. If one of the feedstocks (alcohol or carboxylic acid) has a lower boiling point than the ester formed and forms a miscibility gap with water, it is possible to use a reactant as azeotroping agent and recycle it back into the mixture after water has been removed. In the case of esterification of higher aliphatic carboxylic acids, aromatic acids or di- or polybasic carboxylic acids, the alcohol used is generally the azeotroping agent.

If the alcohol used serves as azeotroping agent, the procedure is typically to at least partly condense the vapor from the reactor, to separate the condensate into an aqueous phase and an organic phase consisting essentially of the alcohol used for the esterification, and to recycle the organic phase at least partly into the reactor.

EP-A 1 186 593 describes a process for preparing carboxylic esters by reacting di- or polycarboxylic acids or anhydrides thereof with alcohols, wherein the water of reaction is removed by azeotropic distillation with the alcohol. The amount of liquid removed from the reaction by the azeotropic distillation is made up again completely or partly by the alcohol.

WO 2010/076192 A1 proposes removing low boilers from the organic phase to be recycled in order to prevent the accumulation thereof in the reactor system.

U.S. Pat. No. 7,276,621 B2 describes a process for titanate-catalyzed esterification of terephthalic acid with 2-ethylhexanol. An inert gas is passed through the reaction mixture in order to promote the removal of water.

JP 4956945 B2 also describes a process for esterification of terephthalic acid with 2-ethlhexanol. In this case, the terephthalic acid is introduced into the reaction system continuously or batchwise as a slurry. The metered addition is effected at the same rate at which the terephthalic acid is converted to the product.

U.S. Pat. No. 7,799,942 B2 describes a process for preparing terephthalic diesters in a reactor at atmospheric pressure using a distillation column atop the reactor. In addition, an inert gas flows through the reaction mixture.

WO 2010/076193 A1 describes a process for purifying the crude ester product of an esterification reaction, in which a metallic esterification catalyst is used.

The solubility of terephthalic acid in higher alcohols is low. For example, terephthalic acid is soluble in 2-ethlhexanol at 180° C. only to an extent of less than 0.65% by weight. The reaction of terephthalic acid with higher alcohols proceeds only via the proportion of terephthalic acid present dissolved in the alcohol. For the attainment of high conversions, it is essential to ensure constant mixing of the heterogeneous mixture of terephthalic acid and alcohol, and effective introduction of heat into the reaction system. In addition, it is important to keep the water content in the reaction mixture low, in order to be able to shift the reaction equilibrium to the product side and, if hydrolysis-sensitive esterification catalysts are used, to prevent the hydrolysis of the catalyst. The metered addition of solid terephthalic acid into the reactor containing boiling alcohol, for example via a conveying screw, in which the powder drops into the reactor in freefall at the free end of the screw, is possible only with difficulty because of the risk of the terephthalic acid forming lumps. In the case of tall reactors of high volume, the arrangement of a reservoir vessel for terephthalic acid above the reactor is often associated with construction difficulties.

It is therefore an object of the invention to provide a process for preparing terephthalic diesters which allows simple introduction of the terephthalic acid into the reactor, enables effective mixing of the reaction mixture and achieves effective introduction of heat into the reaction system and full conversion of the terephthalic acid. It is a further object of the invention to provide a process which can be performed in existing reactors for esterification reactions through minor retrofitting.

The present invention therefore provides a process for preparing a terephthalic diester by reacting terephthalic acid with at least one alcohol, wherein
  a) terephthalic acid is suspended in the alcohol in a dispersing tank to obtain a preliminary suspension,
  b) the preliminary suspension is passed from the dispersing tank into a reactor and converted in the presence of an esterification catalyst,
  c) a reaction suspension is drawn off from a region between the upper region and the lower region of the reactor, the reaction suspension drawn off is divided, a first stream of the reaction suspension is recycled into the upper region of the reactor and a second stream of the reaction suspension is introduced into the lower region of the reactor, and the reaction suspension is thus mixed,
  d) wherein the stream drawn off and/or the first stream is passed through a heat exchanger outside the reactor and heated; and
  e) water of reaction is distilled off together with the vapor as alcohol-water azeotrope, the vapor is at least partly condensed, the condensate is separated into an aqueous phase and an organic phase and the organic phase is at least partly recycled into the reaction system.

A BRIEF DESCRIPTION OF THE FIGURE

Figure 1:
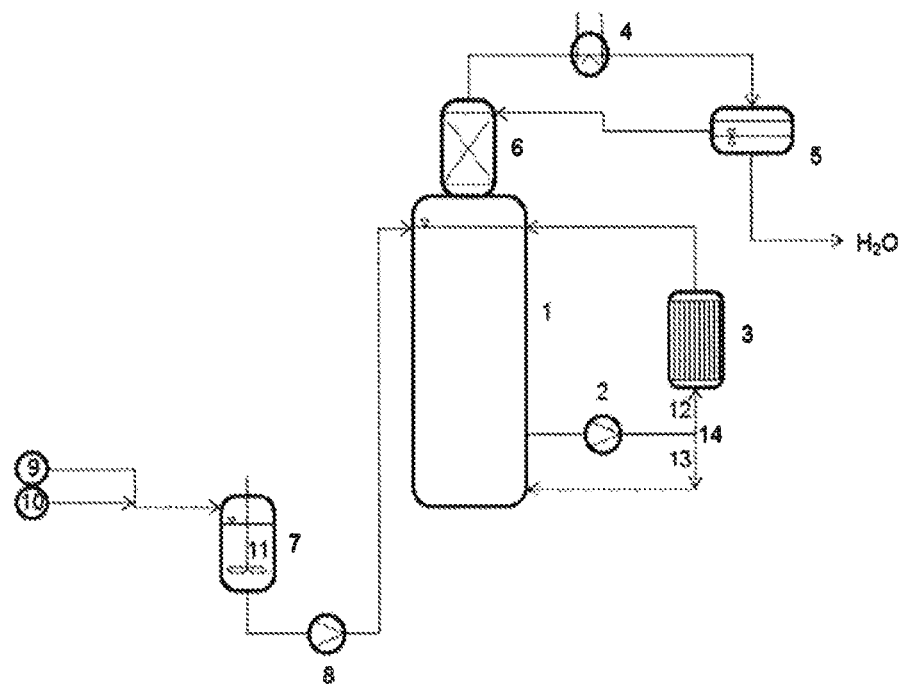
FIG. 1 shows a plant suitable for performing the process according to the invention.

The process according to the invention can be performed batchwise or continuously, but is preferably performed batchwise.

The process gets around the problems associated with the metered addition of solid terephthalic acid into the reactor, such as formation of terephthalic acid lumps and blockage of the conveying screw or another conveying unit. The process provides for the preparation of a preliminary suspension in a dispersing tank. Terephthalic acid is metered into the reactor not in solid form but in the form of a suspension.

The preliminary suspension is prepared by suspending pulverulent terephthalic acid in a portion of the alcohol in the dispersing tank. For this purpose, a suitable mixing apparatus is used. For instance, an amount of the terephthalic acid can be mixed with alcohol using a stirrer; alternatively, dispersing pumps can be used. For example, the total amount of terephthalic acid can be suspended in one step, or the terephthalic acid can be suspended in portions over the course of the process. For the suspension in portions, it is possible to meter terephthalic acid into the dispersing tank, for example, with the aid of a conveying screw.

The mixing can also be effected in a closed chamber through the interaction of a rotating rotor and a stator, in which case only an incremental amount of the components is continuously mixed together in each case, and the suspension then leaves the chamber.

The alcohol used to prepare the preliminary suspension may be fresh alcohol and/or return alcohol, i.e. the organic phase which is obtained after condensation of the vapor and phase separation of the condensate.

The dispersing tank usually consists of metallic materials, preference being given to stainless steel. The dispersing tank can be connected to the reactor on the gas side.

The preliminary suspension is passed into the reactor using a pump or by means of gravity. Usable pumps are in principle all the conveying pumps known to those skilled in the art that are regarded as suitable in view of the properties of the preliminary suspension to be conveyed. Conveying pumps usable with preference are a centrifugal pump, piston pump, screw pump, impeller pump or peristaltic pump. The preliminary suspension can be metered into the reactor in portions or continuously. The metered addition is preferably effected continuously. The preliminary suspension can in principle be metered in at any point in the reactor, but preference is given to adding the preliminary suspension in the upper region of the reactor, especially above the liquid level in the reactor. In this way, backflow counter to the direction of metered addition can very substantially be prevented.

The reactor may be any reactor suitable for performance of chemical reactions in the liquid phase. Suitable reactors are non-backmixed reactors such as tubular reactors or delay vessels provided with internals, but preferably backmixed reactors such as stirred tanks, loop reactors, jet loop reactors or jet nozzle reactors. Optionally, it is also possible to combine a plurality of reactors in a multistage apparatus. Reactors of this kind are, for example, loop reactors with installed sieve trays, cascaded vessels, tubular reactors with intermediate feeding or stirred columns.

Preference is given to using a stirred tank reactor. Stirred tank reactors usually consist of metallic materials, preference being given to stainless steel.

Especially preferred is the use of existing reaction systems which are utilized, for example, for the esterification of phthalic anhydride and can be used for the esterification of terephthalic acid through minor retrofitting. Retrofitting operations are necessary, relating particularly to the provision of a dispersing tank, of a lateral draw in the reactor and of a stream divider for division of the stream of the reaction suspension drawn off.

In the reactor, the preliminary suspension and the esterification catalyst are brought into contact, which gives a reaction suspension. In one embodiment of the process, i) the preliminary suspension is passed into the unfilled reactor, ii) the preliminary suspension is heated to boiling and iii) the esterification catalyst is added. Optionally, the sequence of steps ii) and iii) can be reversed.

In a preferred embodiment of the process, however, the esterification catalyst is initially charged in the reactor in a portion of alcohol, for example 15-50% of the total amount of alcohol, preferably 25-40%. The catalyst/alcohol mixture can first be heated to boiling and then the metered addition of the preliminary suspension can be started. Alternatively, the preliminary suspension is added to the catalyst/alcohol mixture and then heated. Optionally, the heating of the catalyst/alcohol mixture and the metered addition of the preliminary suspension can be performed in parallel.

During the reaction, the reaction suspension in the reactor has a temperature close to the boiling point of the reaction mixture, for example a temperature of 150° C. to 250° C., preferably of 185° C. to 220° C. The boiling point of the reaction suspension is dependent on the ratio of terephthalic diester to alcohol and rises over the course of the reaction.

A stream of the reaction suspension is drawn off from the reactor in a region between the upper and lower regions of the reactor. The draw point is preferably chosen such that, in the event of failure of the circulation pump, suspended terephthalic acid collects beneath the draw. The stream of the reaction suspension drawn off is divided, for example by means of a controllable flow divider, into a first stream and a second stream. The stream of the reaction suspension which is drawn off from the reactor is generally divided into the first and second streams in a ratio of 1:10 to 10:1.

Usable pumps are in principle all the conveying pumps known to those skilled in the art that are regarded as suitable for performing the process according to the invention in view of the properties of the reaction suspension to be conveyed. Conveying pumps usable with preference are a centrifugal pump, piston pump, screw pump, impeller pump or peristaltic pump. Very particular preference is given to an axial or radial centrifugal pump.

The provision of the draw in a region as defined above can prevent terephthalic acid from settling out in the circulation pump. In the event of disrupted operation, for example the failure of the circulation pump, this facilitates the restart of the circulation pump.

According to the invention, heat is introduced into the reaction system by passing the stream drawn off from the reactor, before it is divided, and/or the first stream through a heat exchanger outside the reactor and heating it.

In one embodiment, the stream of the reaction suspension drawn off from the reactor, before it is divided, is passed through a heat exchanger outside the reactor and heated. The heated reaction suspension is divided, a first stream of the reaction suspension is recycled into the upper region of the reactor and a second stream of the reaction suspension is introduced into the lower region of the reactor, and the reaction suspension is thus mixed. Both the first and second streams contribute to heating of the reactor contents; the second stream contributes to mixing.

In one embodiment, the stream of the reaction suspension drawn off from the reactor is divided, and a first stream of the reaction suspension is passed through a heat exchanger outside the reactor and heated and recycled into the upper region of the reactor. A second stream of the reaction suspension is introduced into the lower region of the reactor and the reaction suspension is thus mixed.

The first stream of the reaction suspension is recycled into the reactor in the upper region of the reactor, for example at the height of the liquid level of the reaction suspension or in the range from the height of the liquid level of the reaction suspension to 30% below it.

The volume flow rate of the reaction suspension drawn off is chosen, for example, such that the complete reactor contents are circulated within a period of 1 to 60 minutes, preferably 1 to 10 minutes. The constant circulation of the reactor contents assures effective mixing of the reaction suspension.

Preferably, the stream of the reaction suspension is run through the heat exchanger outside the reactor counter to the direction of gravity, i.e. from the bottom upward. The specified direction of the stream counter to gravity prevents sedimentation of terephthalic acid in the heat exchanger.

The reaction suspension is heated by the passage through a heat exchanger to a temperature at which a sufficiently large vapor flow rate arises at the surface of the reaction mixture to discharge the water of reaction, for example to a temperature of 150 to 250° C., preferably 180 to 220° C.

The second stream of the reaction suspension is introduced into the lower region of the reactor below the draw, preferably in a region between the reactor base and 5% above the reactor base, based on the total height of the reactor, and the reaction suspension is thus mixed. The second stream of the reaction suspension which is metered back into the reactor serves to mix the reaction suspension and to prevent sedimentation of terephthalic acid at the base of the reactor. Sedimented terephthalic acid is not available for the esterification reaction. The metered addition of the second stream beneath the liquid level agitates any sedimented terephthalic acid and allows it to be converted back to suspension.

Optionally, the mixing of the reaction suspension can be promoted by the metered addition of an inert gas into the reactor, especially at the lowest point in the reactor, and/or the stream of the reaction suspension. Especially in the event of disrupted operation of the pump for the drawing-off of the reaction suspension, for example in the event of failure of the pump, the metered addition of the inert gas contributes to preventing sedimentation of terephthalic acid at the base of the reactor and/or in pipelines. Preferably, the inert gas is metered in on the suction side of the pump. Alternatively, the metered addition can be effected on the pressure side of the pump. This enables maintenance of the circulation through the heat exchanger. Inert gases are all gases which do not have any reactivity with the constituents of the reaction suspension under the reaction conditions, especially nitrogen or argon. Preferably, the inert gas is metered in in an amount of 0.01 to 5 units by volume of the inert gas per unit by volume of the reaction suspension per hour.

During the reaction, an alcohol-water azeotrope is distilled off together with the vapor, the vapor is at least partly condensed, the condensate is separated into an aqueous phase and an organic phase and the organic phase is at least partly recycled into the reactor.

Condensation or partial condensation of the vapor can be effected using any suitable condensers. These can be cooled with any desired cooling media. Condensers with air cooling and/or water cooling are preferred, and air cooling is particularly preferred.

The condensate obtained is subjected to a phase separation into an aqueous phase and an organic phase. For this purpose, the condensate is typically passed into a phase separator (decanter), where it divides into two phases as a result of mechanical settling, and these can be drawn off separately. The aqueous phase is removed and, optionally after workup, can be discarded or used as stripping water in the aftertreatment of the ester.

The aqueous phase is recycled into the reactor through a column (called return alcohol column) in which the recycled organic phase is run counter to at least a portion of the vapor. The return alcohol column may, for example, be a tray column, column with structured packing or column with random packing. A small number of plates is generally sufficient. A suitable example is a column having 2 to 10 theoretical plates. Preferably, the column is placed atop the reactor, i.e. connected directly to the reactor. Appropriately, the organic phase is introduced into the return alcohol column at the top or in the upper region. The condensate running off from the return alcohol column passes back into the reactor. The recycling of the organic phase via the return alcohol column has the advantage that the recycled organic phase is preheated and freed of traces of water which have remained in the organic phase after the phase separation or are dissolved in the organic phase in accordance with their thermodynamic solubility. The water content in the recycled organic phase is less than the maximum solubility of water in the alcohol, preferably less than 3% by weight, especially less than 0.5% by weight.

In the process according to the invention, preference is given to using linear, branched or cyclic aliphatic alcohols having 4 to 18 carbon atoms, especially 8 to 14 carbon atoms, or aromatic alcohols. The alcohols are monools and/or polyols and may be tertiary, secondary or primary.

The alcohols used may originate from various sources. Suitable feedstocks are, for example, fatty alcohols, alcohols from the Alfol process, or alcohols or alcohol mixtures which have been obtained by hydrogenating saturated or unsaturated aldehydes, especially those whose synthesis includes a hydroformylation step.

Alcohols which are used in the process according to the invention are, for example, n-butanol, isobutanol, pentanols, hexanols, heptanols, octanols such as n-octanol, 2-ethylhexanol, nonanols, decyl alcohols or tridecanols, prepared by hydroformylation or aldol condensation and subsequent hydrogenation. The alcohols can be used as a pure compound, as a mixture of isomeric compounds or as a mixture of compounds having different numbers of carbon atoms. One example of such an alcohol mixture is a $C_9/C_{11}$ alcohol mixture.

Aromatic alcohols which can be used in the process according to the invention are, for example, phenol, benzyl alcohol, 1-naphthol, 2-naphthol, 1,2-dihydroxybenzene, 1,3-dihydroxybenzene, 1,4-dihydroxybenzene, 1,4-naphthohydroquinone, 2,4,6-trinitrophenol, primary phenylethyl alcohol, secondary phenylethyl alcohol, phenylpropyl alcohol, o-tolyl alcohol, p-tolyl alcohol, cuminic alcohol, p-nitrophenol, m-, o- or p-alkylphenol, e.g. m-, o- or p-methylphenol or m-, o- or p-ethylphenol, m-, o- or p-halophenol, e.g. m-, o- or p-chlorophenol or m-, o- or p-bromophenol. In addition, it is possible to use p-nitrobenzyl alcohol, m-, o- or p-alkylbenzyl alcohol, e.g. m-, o- or p-methylbenzyl alcohol or m-, o- or p-ethylbenzyl alcohol, m-, o- or p-halobenzyl alcohol, e.g. m-, o- or p-chlorobenzyl alcohol or m-, o- or p-bromobenzyl alcohol, 2-ethoxyphenol, 3-ethoxyphenol, 4-ethoxyphenol, 2-propoxyphenol, 3-propoxyphenol, 4-propoxyphenol, 2-ethoxybenzyl alcohol, 3-ethoxybenzyl alcohol, 4-ethoxybenzyl alcohol, 2-propoxybenzyl alcohol, 3-propoxybenzyl alcohol or 4-propoxybenzyl alcohol.

Polyols which can be used in the process according to the invention are, for example, propane-1,2-diol, propane-1,3-diol, butane-1,2-diol, butane-1,3-diol, butane-1,4-diol, neopentyl glycol, pentane-1,5-diol, hexane-1,6-diol, decane-1,10-diol, diethylene glycol, 2,2,4-trimethylpentane-1,5-diol, 2,2-dimethylpropane-1,3-diol, 1,4-dimethylolcyclohexane, 1,6-dimethylolcyclohexane, glycerol, trimethylolpropane, erythritol, pentaerythritol and sorbitol.

Particularly preferred alcohols are 2-ethlhexanol, 2-propylheptanol, isononanol isomer mixtures, decanol isomer mixtures and $C_9/C_{11}$ alcohol mixtures.

The alcohol to be converted, which serves as azeotroping agent, can be used in a stoichiometric excess. Preferably, the amount of alcohol used is selected such that 10% to 35% by weight of alcohol is present in the crude product of the reaction, based on the theoretical full conversion of the terephthalic acid.

The inventive esterification is conducted in the presence of an esterification catalyst.

In a preferred embodiment of the process according to the invention, the esterification catalyst is soluble in the alcohol.

The esterification catalyst is suitably selected from Lewis acids such as alkoxides, carboxylates and chelate compounds of titanium, zirconium, hafnium, tin, aluminum and zinc; boron trifluoride, boron trifluoride etherates; mineral acids such as sulfuric acid, phosphoric acid; sulfonic acids such as methanesulfonic acid and toluenesulfonic acid, and ionic fluids.

Suitably, the esterification catalyst is selected from alkoxides, carboxylates and chelate compounds of titanium, zirconium, hafnium, tin, aluminum and zinc. Suitable substances include tetraalkyl titanates such as tetramethyl titanate, tetraethyl titanate, tetra-n-propyl titanate, tetraisopropyl titanate, tetra-n-butyl titanate, tetraisobutyl titanate, tetra-sec-butyl titanate, tetraoctyl titanate, tetra(2-ethylhexyl) titanate; dialkyl titanates ($(RO)_2TiO$ in which R is, for example, isopropyl, n-butyl, isobutyl) such as isopropyl n-butyl titanate; titanium acetylacetonate chelates, such as diisopropoxybis(acetylacetonate)titanate, diisopropoxybis(ethylacetylacetonate)titanate, di-n-butylbis(acetylacetonate)titanate, di-n-butylbis(ethylacetoacetate)titanate, triisopropoxybis(acetylacetonate)titanate; zirconium tetraalkoxides, such as zirconium tetraethoxide, zirconium tetrabutoxide, zirconium tetrabutyrate, zirconium tetrapropoxide, zirconium carboxylates such as zirconium diacetate; zirconium acetylacetonate chelates such as zirconium tetra(acetylacetonate), tributoxyzirconium acetylacetonate, dibutoxyzirconium bis(acetylacetonate); aluminum trisalkoxides such as aluminum triisopropoxide, aluminum trisbutoxide; aluminum acetylacetonate chelates such as aluminum tris(acetylacetonate) and aluminum tris(ethylacetylacetonate). More particularly, isopropyl n-butyl titanate, tetra(isopropyl) orthotitanate or tetra(butyl) orthotitanate or mixtures thereof are used.

Suitable ionic fluids (ionic liquids) are, for example, methylimidazcliumbutanesulfonic acid triflate and 1-ethyl-3-methylimidazolium hydrogensulfate.

The catalyst concentration depends on the type of catalyst. In the titanium compounds used with preference, it is 0.001 to 1.0 mol % based on the amount of terephthalic acid, especially from 0.01 to 0.2 mol %.

The reaction temperatures are between 150° C. and 250° C. The optimal temperatures depend on the feedstocks, progress of the reaction and catalyst concentration. They can be determined easily by experiments for each individual case Higher temperatures increase the reaction rates and promote side reactions, for example olefin formation or formation of colored by-products. It is necessary for removal of the water of reaction that the alcohol can be distilled out of the reaction mixture. The desired temperature or the desired temperature range can be established via the pressure in the reactor. In the case of low-boiling alcohols, therefore, the reaction can be performed at elevated pressure, and in the case of higher-boiling alcohols under reduced pressure. For example, in the reaction of terephthalic acid with 2-ethlhexanol, a temperature range from 180° C. to 220° C. is employed within the pressure range from 300 mbar to 2 bar.

Appropriately, the reactor and dispersing tank will be operated at essentially the same pressure, especially about ambient pressure. Optionally, the reactor and dispersing tank can also be operated at different pressures.

Preference is given to performing the process according to the invention until the terephthalic acid has been essentially fully converted. The conversion can be determined via the determination of the acid number of the reaction suspension. The acid number is determined by neutralizing a sample of the reaction suspension with tetrabutylammonium hydroxide. The mass of tetrabutylammonium hydroxide consumed in the neutralization can be used to determine the molar amount of tetrabutylammonium hydroxide consumed, and stoichiometric considerations to determine the molar amount of free acid groups in unconverted terephthalic acid. Proceeding from the known molar amount of terephthalic acid used, it is thus possible to determine the conversion. Additional methods for determining the conversion are HPLC analyses and the measurement of the turbidity of the reaction suspension by inline turbidity measurements. In the process according to the invention, a conversion greater than 99% is preferably achieved.

After the reaction has ended, the reaction mixture consisting essentially of the desired ester and excess alcohol comprises, as well as the catalyst and/or conversion products thereof, small amounts of ester carboxylic acid(s) and/or unconverted carboxylic acid.

These crude ester mixtures are worked up by admixing the crude di($C_4$-$C_{18}$-alkyl) terephthalate with an aqueous base, evaporating water out of the mixture obtained, admixing the liquid phase obtained with water to form a water-in-oil emulsion, distilling water out of the emulsion and filtering the di($C_4$-$C_{18}$-alkyl) terephthalate.

First of all, the esterification catalyst is deactivated and precipitated by adding an aqueous base. At the same time, the acid and/or partial ester of the acid unconverted in the esterification reaction are converted to salts.

The aqueous base can be added in any suitable manner. It is preferably added beneath the liquid surface of the crude ester. Suitable apparatus for this purpose include, for example, probes and nozzles provided at one end of the vessel or the vessel wall. The mixture is then mixed vigorously, for example by means of a stirrer or circulation pump.

The amount of aqueous base added should be such that it is sufficient for complete neutralization of the acidic components of the crude ester. In practice, a greater or lesser excess of base is used. The total amount of the acidic components of the crude ester is appropriately detected via the acid number (in mg KOH/g). Preference is given to introducing 100% to 300% neutralization equivalents with the aqueous base, based on the acid number of the crude ester, especially 130% to 220%. A neutralization equivalent is understood to mean the amount of base that can bind the same number of protons as 1 mg of KOH. In other words, an excess of base of up to 200% is used, preferably 30% to 120%.

Useful aqueous bases include solutions of hydroxides, carbonates, hydrogencarbonates of alkali metals and alkaline earth metals. Aqueous alkali metal hydroxide solutions are generally preferred. Aqueous sodium hydroxide solution is particularly preferred because of its ease of availability.

The concentration of the aqueous base is not critical per se, but there may be hydrolysis of the esters at the site of introduction of the base when concentrated alkali solutions are used. On the other hand, the concentration of the aqueous base should not be too low, since the water introduced with the aqueous base has to be removed again in the subsequent step. Therefore, preference is given to aqueous bases of moderate to low concentration, for example those of a concentration of 0.5% to 25% by weight, especially 1% to 10% by weight. Aqueous sodium hydroxide solution having a concentration of 1% to 5% by weight is particularly preferred.

Often, the precipitated solid consisting essentially of catalyst breakdown products and salts of unconverted acid or partial esters of polybasic acids is present in finely divided form and is difficult to filter. Appropriately, the fine particles are agglomerated to larger, readily removable particles.

For this purpose, the liquid phase is admixed with water to form a water-in-oil emulsion. The water is distributed as a disperse phase in the form of fine droplets in the liquid organic phase. The fine solid particles migrate to the interface between water droplets and surrounding organic phase. In the course of the subsequent evaporation of the water, the fine particles agglomerate and form coarse, efficiently removable particles.

In order that a separate water phase forms, the amount of water added must be greater than that corresponding to the solubility of water in the organic phase. One factor on which the water solubility in the organic phase depends is the content of unconverted alcohol, since the alcohol acts as a solubilizer. The higher the alcohol content, the more water has to be added to form an emulsion. In the case of typical residual alcohol contents of 20% to 30% by weight, suitable amounts are generally from 20 to 80 g of water, preferably 30 to 60 g, based on 1 kg of crude ester.

The water phase is divided into fine droplets with a suitable stirrer or homogenizer, or by pumped circulation of the emulsion using a circulation pump. The water droplets produced preferably have a mean droplet size of less than 1000 μm. Examples of suitable stirrers having a high specific stirrer input are disk stirrers. Alternatively, particularly in the case of a continuous process regime, it is possible to use a mixing nozzle in which water is added directly to the crude ester stream via a dispersing valve.

The emulsion is appropriately formed at about standard pressure.

The water in the emulsion thus produced is distilled off again in the next step.

After this treatment, the solids are in efficiently filterable form; no fines fraction passes through in the filtration. Suitable filters for filtration of the ester are all suitable filters such as chamber filter presses, belt filters, cartridge filters or pan filters. For a continuous process regime, pan filters with centrifugal cake ejection are particularly suitable. The solids removed are discarded.

After the filtration, the ester can be subjected to various aftertreatments, such as a steam stripping or the like.

The invention is illustrated in detail by the appended figures.

FIG. 1 shows a plant suitable for performing the process according to the invention.

According to FIG. 1, alcohol from the reservoir 9 and terephthalic acid from the reservoir 10 are metered into a dispersing tank 7 and mixed to form a preliminary suspension using a stirrer 11. The preliminary suspension is passed into the upper region of the reactor 1 with the aid of a pump 8. Within the reactor 1 are a further portion of the alcohol and the esterification catalyst. At a point in the reactor 1 between the upper and lower regions of the reactor, the reaction suspension is drawn off using a pump 2. The reaction suspension drawn off we divided at a two-way device 14 in a first stream 12 and a second stream 13. The stream 12 is conducted through a heat exchanger 3 outside the reactor. The reaction suspension heated in the heat exchanger 3 is recycled back into the reactor 1 in the upper region thereof. Stream 13 is recycled into the reactor in the lower region of the reactor. The vapor passes through the column 6 and is at least partly condensed in the condenser 4. In the phase separator 5, the condensate is separated into an aqueous phase and an organic phase. The aqueous phase is discarded; the organic phase is recycled into the reactor via column 6.

Figure 2:
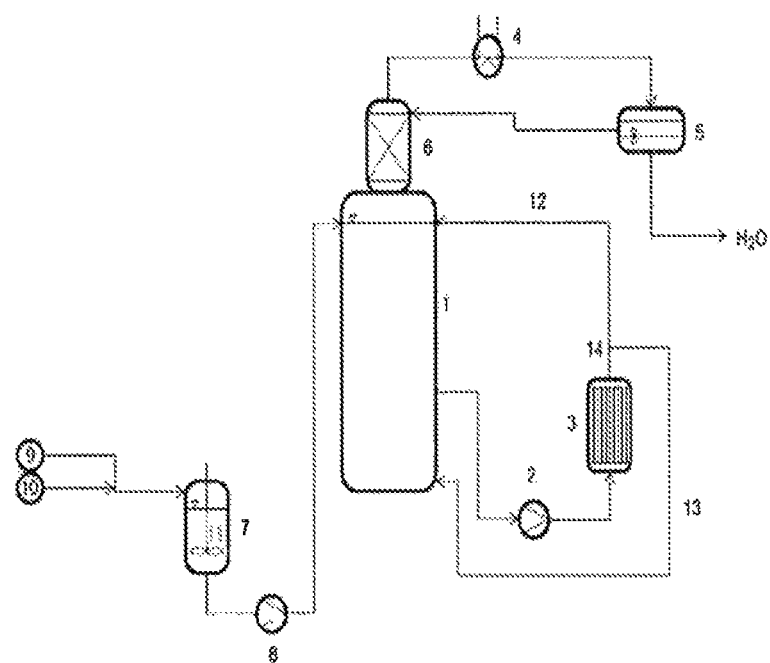
FIG. 2 shows a further plant suitable for performing the process according to the invention.

FIG. 2 shows a further plant suitable for performing the process according to the invention.

In FIG. 2, identical elements that work in the same way bear the same reference numerals as in FIG. 1. The difference from FIG. 1 is that the entire stream of the reaction suspension drawn off from the pump 2 is conducted through the heat exchanger 3. The heated reaction suspension is divided at a two-way device 14 into a first stream 12 and a second stream 13. Stream 12 is recycled back into the reactor 1 in the upper region thereof. Stream 13 is recycled into the reactor in the lower region of the reactor.

The invention claimed is:

1. A process for preparing a terephthalic diester which comprises reacting terephthalic acid with at least one alcohol, wherein
   a) suspending terephthalic acid in the alcohol in a dispersing tank to obtain a preliminary suspension,
   b) passing the preliminary suspension from the dispersing tank into a reactor and converted in the presence of an esterification catalyst,
   c) drawing off a reaction suspension from a region between the upper region and the lower region of the reactor, the reaction suspension drawn off is divided, a first stream of the reaction suspension is recycled into the upper region of the reactor and a second stream of the reaction suspension is introduced into the lower region of the reactor, and the reaction suspension is thus mixed,
   d) wherein the stream drawn off and/or the first stream is passed through a heat exchanger outside the reactor and heated,
   e) distilling off water of reaction together with the vapor as alcohol-water azeotrope, the vapor is at least partly condensed, the condensate is separated into an aqueous phase and an organic phase and the organic phase is at least partly recycled into the reaction system and
   f) preparing the terephthalic diester.

2. The process according to claim 1, wherein the organic phase recycled has a water content lower than the solubility of water in the alcohol.

3. The process according to claim 1, wherein the organic phase passed into the reactor has a water content of less than 3% by weight.

4. The process according to claim 1, wherein the esterification catalyst is a Lewis acid, mineral acid, sulfonic acid or ionic fluid.

5. The process according to claim 4, wherein the esterification catalyst is selected from the group consisting of
alkoxide;
carboxylate or chelate compounds of titanium, zirconium, hafnium, tin, aluminum or zinc;
boron trifluoride;
boron trifluoride etherates;
sulfuric acid;
phosphoric acid;
methanesulfonic acid and
toluenesulfonic acid.

6. The process according to claim 1, wherein the esterification catalyst is selected from the group consisting of
a) acidic ion exchangers;
b) zeolites;
c) oxides of magnesium, aluminum, zinc, titanium, silicon, tin, lead, antimony, bismuth, molybdenum or manganese
d) hydroxides of magnesium, aluminum, zinc, titanium, silicon, tin, lead, antimony, bismuth, molybdenum or manganese and
e) mixtures of c) and d) above.

7. The process according to claim 1, wherein the esterification catalyst is soluble in the alcohol.

8. The process according to claim 1, wherein the alcohol is a linear aliphatic $C_4$-$C_{18}$ alcohol, a branched aliphatic $C_4$-$C_{18}$ alcohol, cyclic aliphatic $C_4$-$C_{18}$ alcohol or an aromatic alcohol.

9. The process according to claim 1, which is performed continuously or batchwise.

10. The process according to claim 1, wherein the reaction in the reactor is conducted at a temperature of 100 to 250° C.

11. The process according to claim 1, wherein the alcohol is used in such a stoichiometric excess that the crude esterification product comprises 15% to 35% by weight of alcohol.

12. The process according to claim 1, wherein an inert gas is metered into the reactor and/or the stream of the reaction suspension for fluidization.

13. The process according to claim 1, wherein the crude terephthalic diester is worked up by admixing with an aqueous base, evaporating water out of the mixture obtained, admixing the liquid phase obtained with water to form a water-in-oil emulsion, distilling water out of the emulsion and filtering the terephthalic diester.

14. The process according to claim 1, wherein the volume flow rate of the reaction suspension drawn off is chosen such that the reactor contents are circulated completely within a period of 1 to 10 minutes.

* * * * *